US008338634B2

(12) United States Patent
Deng et al.

(10) Patent No.: US 8,338,634 B2
(45) Date of Patent: Dec. 25, 2012

(54) CATALYST FOR THE SYNTHESIS OF ALKYL CARBAMATES, THE METHOD FOR PREPARING THE SAME AND THE USE THEREOF

(75) Inventors: Youquan Deng, Gansu (CN); Yubo Ma, Gansu (CN); Liguo Wang, Gansu (CN); Xiaoguang Guo, Gansu (CN); Shiguo Zhang, Gansu (CN); Yude He, Gansu (CN); Stefan Wershofen, Monchengladbach (DE); Stephan Klein, Shanghai (CN); Zhiping Zhou, Shanghai (CN)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 12/918,848

(22) PCT Filed: Feb. 13, 2009

(86) PCT No.: PCT/EP2009/001008
§ 371 (c)(1),
(2), (4) Date: Aug. 23, 2010

(87) PCT Pub. No.: WO2009/106237
PCT Pub. Date: Sep. 3, 2009

(65) Prior Publication Data
US 2011/0160478 A1  Jun. 30, 2011

(30) Foreign Application Priority Data
Feb. 26, 2008 (CN) .......................... 2008 1 0033898

(51) Int. Cl.
*C07C 261/00* (2006.01)
*C07C 269/00* (2006.01)
*C07C 271/00* (2006.01)
*B01J 23/00* (2006.01)
*B01J 21/00* (2006.01)

(52) U.S. Cl. ........ 560/157; 502/240; 502/242; 502/300; 502/351; 502/439

(58) Field of Classification Search .................. 560/157; 502/240, 242, 300, 350, 439
See application file for complete search history.

(56) References Cited

U.S. PATENT DOCUMENTS

| | | | |
|---|---|---|---|
| 2,537,561 A | 6/1958 | Beinfest et al. | |
| 3,013,064 A | 12/1961 | Beinfest et al. | |
| 3,574,711 A | 4/1971 | Robeson | |
| 3,702,320 A * | 11/1972 | Fritok et al. ................... | 528/371 |
| 4,242,520 A | 12/1980 | Moy | |
| 4,258,201 A * | 3/1981 | Moy ............................... | 560/24 |
| 4,260,781 A * | 4/1981 | Harvey .......................... | 560/24 |
| 4,443,621 A * | 4/1984 | LaMattina et al. ............ | 560/142 |
| 4,472,568 A * | 9/1984 | Rasshofer et al. ............. | 528/68 |
| 4,621,149 A * | 11/1986 | Fukuoka et al. ............... | 560/24 |
| 4,987,248 A * | 1/1991 | Waller .......................... | 560/157 |
| 5,101,062 A * | 3/1992 | Yamada et al. ................. | 560/24 |
| 5,194,660 A * | 3/1993 | Leung et al. .................... | 560/24 |
| 5,463,109 A * | 10/1995 | Nishihira et al. ............. | 560/157 |
| 5,606,096 A * | 2/1997 | Yamanaka et al. ............. | 560/157 |
| 5,892,100 A * | 4/1999 | Yamanaka et al. ............. | 560/157 |
| 5,962,721 A * | 10/1999 | Kim et al. ........................ | 560/24 |
| 6,133,473 A * | 10/2000 | Berrier .......................... | 560/157 |
| 6,140,531 A * | 10/2000 | Govindan et al. ............. | 560/163 |
| 6,410,778 B2 * | 6/2002 | Laqua et al. .................... | 560/115 |
| 7,271,120 B2 | 9/2007 | Sun et al. | |
| 7,405,319 B2 * | 7/2008 | Srinivas et al. ................. | 560/24 |
| 2003/0050498 A1 * | 3/2003 | Bammel et al. ................. | 560/24 |
| 2005/0222450 A1 * | 10/2005 | Gupte et al. ................... | 560/157 |

FOREIGN PATENT DOCUMENTS

CN         1365969 A     8/2002

* cited by examiner

Primary Examiner — Cam N. Nguyen
(74) Attorney, Agent, or Firm — N. Denise Brown

(57) ABSTRACT

The present invention pertains to a catalyst for the synthesis of organic alkyl carbamates, the method for preparing the same and the use thereof. The catalyst comprises a catalytically active component and a catalyst support, and the catalytically active component being carried by the catalyst support, wherein the catalytically active component comprises a transition metal oxide, and the general formula of the transition metal oxide is EOx, wherein E is selected from transition metal element and x is in the range of 0.5-4.

3 Claims, No Drawings

CATALYST FOR THE SYNTHESIS OF ALKYL CARBAMATES, THE METHOD FOR PREPARING THE SAME AND THE USE THEREOF

TECHNICAL FIELD

The present invention pertains to the synthesis of alkyl carbamates, especially a catalyst for the synthesis of organic alkyl carbamates, the method for preparing the same and the use thereof.

BACKGROUND

Alkyl carbamates are widely used to prepare chemical intermediates. For example, methyl carbamate can be used for the synthesis of melamine derivatives, polyethylene amine, furthermore, methyl carbamate can also be reacted with unsaturated hydrocarbons, aldehydes, ketones, multifunctional alcohols and aryl rings to afford various derivatives. Ethyl carbamate can be used to synthesize alkanediol dicarbamates, a promising class of tranquilizing drugs (Sidney Beinfest et al, preparation of organic mono-carbamates, U.S. Pat. No. 2,837,561). Butyl carbamate may be reacted with formaldehyde to form methylol derivates that are effective as textile crease-proofing agents (Max Robeson etc. production of alkyl carbamate, U.S. Pat. No. 3,574,711). In addition, the alkyl carbamates can be used for the synthesis of the corresponding organic carbonates, or be used as new kind of carbonyl sources for the synthesis of isocyanates.

Due to the alkyl carbamates' wide application, the methods for preparing the alkyl carbamates received much concern in the industry. U.S. Pat. No. 4,242,520 disclosed a method for preparing the alkyl carbamates by reacting amine with carbon monoxide and alcohol in the presence of catalyst, however, this method might potentially harm the producers and users' health, due to the fact that the carbon monoxide his a toxic gas.

Alcoholysis of urea is another mature method to produce alkyl carbamates, which produces alkyl carbamates by reacting urea with hydroxyl group containing compounds under suitable reaction conditions, and avoids using carbon monoxide in the preparation. This method can be used in the presence of catalyst, including ZnO disclosed in U.S. Pat. No. 3,574,711, $Cu(OAc)_2$ disclosed in U.S. Pat. No. 2,837,561 and U.S. Pat. No. 3,013,064, a complex of transition metals oxides and acids disclosed in U.S. Pat. No. 3,554,730, the catalyst system of nano-$TiO_2$ and R3N disclosed in CN1365969, and oxides such as MgO, CaO, ZnO, PbO disclosed in CN1475481.

However, the catalysts used in alcoholysis of urea are not so good, due to the fact that the problems of relative low yields of desired products, catalyst separation and catalyst recycling use were not solved well. Therefore, from view of industry practice, it is more and more desirable to develop a kind of catalysts for the synthesis of alkyl carbamates, wherein the catalysts are not only highly effective but also can be easily recovered from the reaction mixture and reused.

CONTENTS OF INVENTION

The objective of this invention is to provide an catalyst for the synthesis of alkyl carbamates, the catalyst comprising a catalytically active component and a catalyst support, and the catalytically active component being carried by the catalyst support, wherein the catalytically active component comprises a transition metal oxide, and the general formula of the transition metal oxide is EOx, wherein E is selected from transition metal element and x is in the range of 0.5-4.

Another objective of this invention is to provide a process for preparing the catalyst for the synthesis of alkyl carbamates, comprising the steps of:

Heating a catalyst support, wherein the heating temperature is 100-1000° C.;

Impregnating the catalyst support in an acidic aqueous solution to obtain a catalyst precursor, the acidic aqueous solution comprising a catalytically active component precursor, the catalytically active component precursor comprising an anhydrous salt of transition metal, or a hydrous salt of transition metal, or an organic derivative of transition metal, wherein the pH value of the acidic aqueous solution is less than or equal to 6;

Calcinating the catalyst precursor to obtain a catalyst, wherein the calcination temperature is 200-1000° C.

Another objective of this invention is to provide a method for the synthesis of organic alkyl carbamates by reacting urea with a hydroxyl group containing compound in the presence of the catalyst.

The advantages of this invention are that, the catalyst provided in this invention can catalyze the synthesis of alkyl carbamates by reacting urea with hydroxyl group containing compound, the reaction is carried out without using carbon monoxide, the reaction conditions are relative mild, the catalytic activity and reaction selectivity are high, the reaction time is relative short, furthermore, the catalyst can be easily separated from the reaction system and reused, especially, suitable for industrial scale-up and industrial application.

MODE OF CARRYING OUT THE INVENTION

In the present invention, the catalytically active component of the catalyst comprises a transition metal oxide, the general formula of the transition metal oxide is EOx, wherein E is selected from transition metal element and x is in the range of 0.5-4.

The transition metal can be selected from, but not limited to, the group including Ti, Zr, Hf, V, Nb, Ta, Cr, Mo, W, Mn, Tc, Re, Fe, Ru, Os, Co, Rh, Ir, Ni, Pd, Pt, Cu, Ag, Au, Cd, Hg. Preferably, Ti, Zr, Hf, V, Nb, Ta, Cr, Mo, W, Mn, Tc, Re, Fe, Ru, Os, Co, Rh, Ir, Ni, Pd, Pt; more preferably, Ti, Zr, Hf, Cr, Mo, W, Ni, Pd, Pt; most preferably, Ti, Cr, Ni.

Specific but not limiting examples of the transition metal oxide are $TiO_x$, $CrO_x$ or $NiO_x$.

The transition metal oxide complex includes two or more of the aforesaid transition metal oxide.

In general, all materials known in the art as catalyst support can be used in this invention. For example, the material of the catalyst support can be selected from, but is not limited to, silica, alumina, $SnO_2$, $TiO_2$.

Specific but not limiting examples of the catalyst are $TiO_x/SiO_2$, $CrOX$—$NiO_x/SiO_2$, $TiO_x$—$CrO_x/SiO_2$.

The shape of the catalyst support is not critical, for example, it can be spherical, cylindrical or irregular.

The catalyst support comprises catalyst support particles.

The average diameter of the catalyst support particle is not critical. Typically, the average diameter of the catalyst support particle is 0.1-10 mm, preferably 1-5 mm, more preferably 2-3 mm.

The pore volume of said catalyst support particle is not critical as well. Typically, the pore volume is 0.01-2 ml/g, preferably 0.01-1, ml/g, more preferably 0.1-0.8 ml/g, and most preferably 0.35-0.45 ml/g.

The BET surface of the support particle is not critical either. Typically, the BET surface of the support particles is less than or equal to 2000 m²/g, preferabl 100-1500 m²/g, more preferably 200-1000 m²/g, and most preferably 750-800 m²/g.

The loading of the catalytically active component on the support is 0.1-30 wt. %, preferably 4-20 wt. %, based on 100 wt. % of the catalyst.

In the present invention, the method for preparing the catalyst comprises the steps of heating, impregnating and calcinating. After the step of impregnating and prior to the step of calcinating, the method can also include a step of drying of the catalyst precursor, the drying temperature is less than or equal to 100° C.

In the heating step of the catalyst support, the heating temperature is 100-1000° C., preferably 300-900° C., and most preferably 400-700° C. The heatingtime is less than or equal to 24 hours, preferably less than or equal to 10 hours, more preferably 1-8 hours, and most preferably 1.5-6 hours. The heating pressure is not critical, preferably, atmospheric pressure. The heating atmosphere is air, oxygen or nitrogen, preferably air or oxygen; and more preferably air.

In the impregnating step, the heated catalyst support is impregnated in an acidic aqueous solution comprising a catalytically active component precursor, wherein the catalytically active component precursor comprises an anhydrous salt of a transition metal, or a hydrous salt of a transition metal, or an organic derivative of a transition metal. The catalytically active component precursor can be selected from; but is not limited to, a halogenide of a transition metal, a hydroxide of a transition metal, nitrate of a transition metal, a sulfate of a transition metal, an acetate of a transition metal, or their mixture, preferably a nitrate of a transition metal. Specific but not limiting examples are $Cr(NO_3)_3 \cdot 9H_2O$ and $Ni(NO_3)_2 \cdot 6H_2O$. The organic derivative of a transition metal can be selected from, but is not limited to, the alkoxide of a transition metal; a specific but not limiting example is $Ti(O\text{—}Bu)_4$.

The pH value of the acidic aqueous solution is less than or equal to 6, preferably 1-4. The pH value of the acidic aqueous solution can be adjusted by addition of aqueous or non-aqueous acids. The aqueous or non-aqueous acids can be selected from, but are not limited to, $HCl$, $HNO_3$, $H_2SO_4$, $H_3PO_4$, or $CH_3COOH$.

The impregnating temperature is not critical, preferably room temperature. The impregnating time is less than or equal to 24 hours, preferably 2-20 hours.

In the calcinating step, the calcinating temperature shall be high enough to transform the catalyst precursor to catalyst, preferably 200-1000° C., more preferably 300-700° C. The calcinating time is not critical, preferably 1-20 hours, more preferably 2-10 hours.

The calcinating step can be carried out either in an inert atmosphere or in an oxidizing atmosphere. The inert atmosphere is selected from, but is not limited to, nitrogen, a noble gas, any non-oxidizing gas, any non-reducing gas or a mixture of two or more of the aforesaid gases; preferably, the inert atmosphere is nitrogen. The oxidizing-atmosphere is selected from, but is not limited to, oxygen or an oxygen containing gas; preferably, the oxygen containing gas is air.

In the present invention, the method for the synthesis of alkyl carbamates is that, the carbamates is synthesized by reacting urea with hydroxyl group containing compound in present of the catalyst provided in this invention.

The purity of the urea suitable for the synthesis of alkyl carbamates is not less than 99.5% by weight.

The hydroxyl group containing compound suitable for the synthesis of alkyl carbamates is characterized by the formula $C_xH_yO_z$, wherein x, y, z are independently selected from the group of natural numbers. The hydroxyl group containing compound contains one or more hydroxyl groups. The hydroxyl group is selected from, but is not limited to, primary, secondary, tertiary hydroxyl groups. The hydroxyl group containing compound can be selected from, but is not limited to, aliphatic alCohols, cycloaliphatic alcohols, alcohols.

The aliphatic alcohol can be selected from, but is not limited to, methanol, ethanol, 1-propanol, 2-propanol, 1-butanol, 2-butanol, tert-butanol, pentanol and its isomers, hexanol and its isomers, their higher homologues or their isomers. Furthermore, the aliphatic alcohol can be selected from, but is not limited to, diols, preferably, ethylene glycol, propylene glycol. The cycloaliphatic alcohol can be selected from, but is not limited to, cyclopentanol, cyclohexanol. The araliphatic alcohol can be selected from, but is not limited to, benzyl alcohol, 1-phenyl ethanol, 2-phenyl ethanol.

Another group of hydroxyl group containing compounds suitable for the synthesis of alkyl carbamates includes the derivatives of the aforesaid hydroxyl groups containing compounds, wherein one or more hydrogen atoms, which is directly connected to a carbon atom of the hydroxyl groups containing compounds, is substituted by one or more substituens. The substituent can be selected from, but is not limited to, fluorine, chlorine, bromine, or iodine.

The amounts of the raw materials can be employed in such a way that, at least 1 mole of hydroxyl group, which comes from the hydroxyl groups containing compound(s), is present for 1 mole of urea. It is preferred to apply an excess, that is, more than 1 mole of hydroxyl groups, which comes from the hydroxyl group containing compound(s), for 1 mole of urea. It is more preferred to apply at least 4 moles of hydroxyl groups, which comes from the hydroxyl group containing compound(s), presents for 1 mole of urea. It is most preferred to apply at least 8 moles of hydroxyl groups, which comes from the hydroxyl group containing compound(s), presents for 1 mole of urea. For 1 mole of urea, the upper limit of the amount of the hydroxyl group containing compound(s) is not critical, however, from an economical point of view, the amount of the hydroxyl groups; which come from the hydroxyl group containing compound(s), should not exceed 40 moles, preferably 25 moles.

In the synthesis of alkyl carbamates, the catalyst can be employed as fixed bed, fluidized bed or slurry.

In the synthesis of alkyl carbamates, it is possible to use any additional solvent which is inert under the reaction conditions. The solvent can be selected from, but is not limited to, aliphatic hydrocarbons, halogenated aromatic, aliphatic hydrocarbons, ionic liquids.

The reaction for the synthesis of alkyl carbamates can be carried out continuously, semi-continuously or batch-wise. The order of the addition of the raw materials and/or the catalyst to the reactor is not critical, and the best way to add the material and/or catalyst can be determined in orienting experiments. Furthermore, the ammonia formed during the reaction can be removed from the reactor by appropriate means continuously or intermittently to shift the reaction equilibrium to the product side.

The reaction temperature of the synthesis of alkyl carbamates is 100-250° C. If the temperature is too low, the reaction rate might be reduced too much; while at a too high reaction temperature, the risk of unwanted side reactions, which significantly reduce yield and/or selectivity, will increase. The preferred range of the reaction temperature is 120-240° C., more preferably 160-220° C.

The reaction pressure of the synthesis of alkyl carbamates is the autogenous pressure developing at the chosen reaction temperature. Alternatively, the pressure can also be modified by adding an inert gas, which can be selected from, but is not limited to, nitrogen, a noble gas, carbon dioxide, or mixtures of two or more of the aforesaid inert gases. Typically, the pressure is about 1-50 atm, preferably about 1-30 atm, and more preferably about 5-20 atm.

The reaction time of the synthesis of alkyl carbamates necessarily depends on other reaction conditions. Typically, the reaction time is less than or equal to 24 hours, preferably less than or equal to 15 hours, more preferably 2-10 hours, and most preferably 3-6 hours.

The amount of catalyst employed in the synthesis of alkyl, carbamates is not critical, but should be sufficient to provide expected reaction rates. Preferably, the weight ratio between catalyst and urea is less than or equal to 1:1, more preferably 0.01:1-0.2:1.

After the reaction is completed, the resulting reaction mixture is removed from the reactor. The process of work-up and/or product isolation can be achieved by distillation, crystallization, filtration or other appropriate techniques/means, or by combination of two or more aforesaid techniques/means.

The catalyst can be easily separated from the reaction system, furthermore, the catalyst can be recovered and reused by means of filtration, sedimentation, decantation, centrifugation, or combination of two or more aforesaid techniques/means.

EXAMPLES

In the present invention, appropriate reactors can be selected from, but are not limited to, stirred reactors, tubular reactors. The tubular reactors can be selected from, but are not limited to, tubular reactors with inserts, tubular reactors without inserts, tubular reactors with mixing elements, tubular reactors without mixing elements, tubular reactors with redispersing elements, tubular reactors without redispersing elements, or combination of two or more aforesaid tubular reactors.

The catalyst supports used in the following examples are $SiO_2$ particles, which can be obtained commercially. The basic characteristics of the $SiO_2$ particles are: pore volume 0135-0.45 ml/g, average pore diameter 2-3 nm, the BET surface is 750-800 $m^2$/g, the average diameter of the beads is 1-2 mm, the accumulate density is 720 g/l, the specific heat is 0.92 KJ/kg° C.

Preparation of the Catalyst

Example 1

About 10 ml 26-27 wt. % aqueous $HNO_3$ was added dropwise into a 100 ml beaker containing 3 ml $C_{16}H_{34}O_4$ Ti. The pH value of the solution was 1-2. Then 10 g $SiO_2$ particles, which were heated at 600° C. for 2 hours, were added into the solution and impregnated at room temperature for 4 hours, a catalyst precursor was obtained. The catalyst precursor was dried at 90° C. for 4 hours and then was calcined at 500° C. in the air for 4 hours. A catalyst A was obtained. The catalyst A comprised 3.5 wt. % Ti.

Example 2

About 10 ml 26-27 wt. % aqueous $HNO_3$ was added dropwise into a 100 ml beaker containing 4 ml $C_{16}H_{34}O_4$ Ti. The pH value of the solution was 1-2. Then 10 g $SiO_2$ particles, which were heated at 600° C. for 2 hours, were added into the solution and impregnated at room temperature for 4 hours, a catalyst precursor was obtained. The catalyst precursor was dried at 90° C. for 4 hours and then was calcined at 500° C. in the air for 4 hours. A catalyst B was obtained. The catalyst B comprised 5 wt. % Ti.

Example 3

About 10 ml 26-27 wt. % aqueous $HNO_3$ was added dropwise into a 100 ml beaker containing 6 ml $C_{16}H_{34}O_4$ Ti. The pH value of the solution was 1-2. Then 10 g $SiO_2$ particles, which were heated at 600° C. for 2 hours, were added into the solution and impregnated at room temperature for 4 hours, a catalyst precursor was obtained. The catalyst precursor was dried at 90° C. for 4 hours and then was calcined at 500° C. in the air for 4 hours. A catalyst C was obtained. The catalyst C comprised 7 wt. % Ti.

Example 4

About 10 ml 26-27 wt. % aqueous $HNO_3$ was added dropwise into a 100 ml beaker containing 4 ml $C_{16}H_{34}O_4$ Ti. Subsequently, 3.85 g $Cr(NO_3)_3.9H_2O$ was added. After the dissolution of the components, the pH value of the solution was 2-3. Then 10 g $SiO_2$ particles, which were heated at 600° C. for 2 hours, were added into the solution and impregnated at room temperature for 4 hours. A catalyst precursor was obtained. The catalyst precursor was dried at 90° C. for 4 hours and then was calcined at 500° C. in the air for 4 hours. A catalyst D was obtained. The catalyst D, namely TiOx-CrOy/$SiO_2$, comprised 4 wt. % Ti and 2.8 wt. % Cr.

Example 5

About 10 ml 26-27 wt. % aqueous $HNO_3$ was added dropwise into a 100 ml beaker containing 4 ml $C_{16}H_{34}O_4$ Ti. Subsequently, 7.69 g $Cr(NO_3)_3.9H_2O$ was added. After the dissolution of the components, the pH value of the solution was 2-3. Then 10 g $SiO_2$ particles, which were heated at 600° C. for 2 hours, were added into the solution and impregnated at room temperature for 4 hours. A catalyst precursor was obtained. The catalyst precursor was dried at 90° C. for 4 hours and then was calcined at 500° C. in the air for 4 hours. A catalyst E was obtained. The catalyst E, namely TiOx-CrOy/$SiO_2$, comprised 3.5 wt. % Ti and 6 wt. % Cr.

Example 6

About 10 ml 26-27 wt. % aqueous $HNO_3$ was added dropwise into a 100 ml beaker containing 4 ml $C_{16}H_{34}O_4$ Ti. Subsequently, 11.54 g $Cr(NO_3)_3.9H_2O$ was added. After the dissolution of the components, the pH value of the solution was 2-3. Then 10 g $SiO_2$ particles, which were heated at 600° C. for 2 hours, were added into the solution and impregnated at room temperature for 4 hours. A catalyst precursor was obtained. The catalyst precursor was dried at 90° C. for 4 hours and then was calcined at 500° C. in the air for 4 hours. A catalyst F was obtained. The catalyst F, namely TiOx-CrOy/$SiO_2$, comprised 3 wt. % Ti and 8.5 wt. % Cr.

Example 7

7.69 g $Cr(NO_3)_3.9H_2O$ and 10 ml $H_2O$ were added into a 100 ml beaker. Subsequently, 2.0 g $Ni(NO_3)_2.6H_2O$ was added. After the dissolution of the components, the pH value of the solution was 3-35. Then 10 g $SiO_2$ particles, which were heated at 600° C. for 2 hours, were added into the solution and impregnated at room temperature for 4 hours. A catalyst precursor was obtained. The catalyst precursor was dried at 90° C. for 4 hours and then was calcined at 500° C. in the air for 4 hours. A catalyst G was obtained. The catalyst G, namely CrOx-NiOy/SiO$_2$, comprised 6 wt. % Cr and 2 wt. % Ni.

Example 8

7.69 g Cr(NO$_3$)$_3$.9H$_2$O and 10 ml H$_2$O were added into a 100 ml beaker. Subsequently, 4.0 g Ni(NO$_3$)$_2$.6H$_2$O was added. After the dissolution of the components, the pH value of the solution was 3-3.5. Then 10 g SiO$_2$ particles, which were heated at 600° C. for 2 hours, were added into the solution and impregnated at room temperature for 4 hours. A catalyst precursor was obtained. The catalyst precursor was dried at 90° C. for 4 hours and then was calcined at 500° C. in the air for 4 hours. A catalyst H was obtained. The catalyst H, namely CrOx-NiOy/SiO$_2$, comprised 5 wt. % Cr and 3.5 wt. % Ni.

Example 9

7.69 g Cr(NO$_3$)$_3$.9H$_2$O and 10 ml H$_2$O were added into a 100 ml beaker. Subsequently, 6.0 g Ni(NO$_3$)$_2$.6H$_2$O was added. After the dissolution of the components, the pH value of the solution was 3-3.5. Then 10 g SiO$_2$ particles, which were heated at 600° C. for 2 hours, were added into the solution and impregnated at room temperature for 4 hours. A catalyst precursor was obtained. The catalyst precursor was dried at 90° C. for 4 hours and then was calcined at 500° C. in the air for 4 hours. A catalyst I was obtained. The catalyst I, namely CrOx-NiOy/SiO$_2$, comprised 4 wt. % Cr and 4.5 wt. % Ni.

Alkyl Carbamates Synthesis

Quantitative analysis of alkyl carbamates was conducted by external standard method by using of an Agilent 6820 GC having a 30 m×0.25 mm×0.33 μm capillary column (FID detector). Quantitative analysis of urea was conducted by a Hitachi. L-2000 HPLC equipped with a UV-VIS detector and a Hypersil C18 column with mobile phase comprising 15% acetonitrile in water. Quantitative analysis of other possible by-products were conducted by a HP 6890/5973 GC-MS with a 30 m×0.25 mm×0.33 μm capillary column and a chemstation containing a NIST Mass Spectral Database.

Example 10

1000 ml methanol, 70 g urea and 7 g catalyst A or B or C, respectively, were successively added into a 2 L stainless steel reaction vessel equipped with a magnetic stirrer and a gas releasing valve. The reaction vessel was sealed and heated to 180° C., and then the reaction were proceeded for 6 hours, the reaction pressure was 2 MPa. During the reaction, ammonia gas formed during the reaction is released 3 times through the gas releasing valve. After 6 hours, the reaction was stopped and the reactor was, cooled to room temperature. The catalyst could be recovered from the resulting solution containing methanol and raw products by filtration. Raw methyl carbamate (MC) was obtained as a solid, when the solution containing methanol and raw products were distilled at 80° C. to remove methanol. The raw MC was dissolved in 80 ml diethyl ether and filtrated to remove the possible excess urea. The solution obtained from the filtration was evaporated at 60° C. to remove the diethyl ether. MC was obtained as a white solid with the purity being more than or equal to 98%. The results are shown in Table 1.

TABLE 1

| Catalyst | Urea conversion | Yield of the raw MC | Yield of the purified MC |
|---|---|---|---|
| A | 94 wt % | 91 wt % | 88 wt % |
| B | 97 wt % | 93 wt % | 90 wt % |
| C | 93 wt % | 90 wt % | 87 wt % |

Example 11

1000 ml butanol, 50 g urea and 5 g catalyst D or E or F, respectively, were successively added into a 2 L stainless steel reaction vessel equipped with a magnetic stirrer and a gas releasing valve. The reaction vessel was sealed and heated to 180° C., and then the reaction were proceeded for 4 hours, the reaction pressure was 1 MPa. During the reaction, ammonia gas formed during the reaction is released 2 times through the gas releasing valve. After 4 hours, the reaction was stopped and the reactor was cooled to room temperature. The catalyst could be recovered from the resulting solution containing butanol and raw products by filtration. Raw butyl carbamate (BC) was obtained as a solid, when the solution containing butanol and raw products were distilled at 120° C. to remove butanol. The raw BC was dissolved in 120 ml diethyl ether and filtrated to remove the possible excess urea. The solution obtained from the filtration was evaporated at 80° C. to remove the diethyl ether. BC was obtained as a white solid with the purity being more than or equal to 98%. The results are shown in Table 2.

The recovered solid catalyst was dried at 80-100° C. for 2-4 hours, and then the resulting catalyst was reused. Aforesaid reaction and recycling were repeated for four times, the results are also shown in Table 2.

TABLE 2

| Catalyst | Urea conversion | Yield of the raw BC | Yield of the purified BC |
|---|---|---|---|
| D | 95 wt % | 92 wt % | 90 wt % |
| E | 98 wt % | 95 wt % | 93 wt % |
| F | 96 wt % | 93 wt % | 91 wt % |
| E$^a$ | 95 wt % | 93 wt % | 91 wt % |

$^a$the catalyst was reused for the fourth time

Example 12

1000 ml ethanol, 70 g urea and 7 g catalyst G or H or I, respectively, were successively added into a 2 L stainless steel reaction vessel equipped with a magnetic stirrer and a gas releasing valve. The reaction vessel was sealed and heated to 180° C., and then the reaction were proceeded for 4 hours, the reaction pressure was 1.5 MPa. During the reaction, ammonia gas formed during the reaction is released 2 times through the gas releasing valve. After 4 hours, the reaction was stopped and the reactor was cooled to room temperature. The catalyst could be recovered from the resulting solution containing ethanol and raw products by filtration. Raw ethyl carbamate (EC) was obtained as a solid, when the solution containing ethanol and raw products were distilled at 100° C. to remove ethanol. The raw EC was dissolved in 100 ml diethyl ether and filtrated to remove the possible excess urea. The solution obtained from the filtration was evaporated at 80° C. to remove the diethyl ether. EC was obtained as a white solid with the purity being more than or equal to 98%. The results are shown in Table 3.

TABLE 3

| Catalyst | Urea conversion | Yield of the raw EC | Yield of the purified EC |
|---|---|---|---|
| G | 94 wt % | 90 wt % | 87 wt % |
| H | 98 wt % | 95 wt % | 93 wt % |
| I | 96 wt % | 92 wt % | 89 wt % |

Although the present invention is illustrated through Examples, it is not limited by these Examples in any way. Without departing from the spirit and scope of this invention, those skilled in the art can make any modifications and alternatives. And the protection of this invention is based on the scope defined by the claims of this application.

The invention claimed is:

1. A method for the synthesis of organic alkyl carbamates by reacting urea with a hydroxyl group containing compound in the presence of a catalyst which comprises a catalytically active component and a catalyst support, wherein said catalytically active component is carried by said catalyst support, said catalytically active component comprises a transition metal oxide, and the transition metal oxide corresponds to the general formula:

$$EO_x$$

wherein:
E represents a transition metal element, and
x represents a number in the range of 0.5-4.

2. The method as claimed in claim 1, wherein the weight ratio of said catalyst and urea is less than or equal to 1:1.

3. The method as claimed in claim 1, wherein the reaction temperature is 100-250° C., the reaction pressure is 1-50 atm, and the reaction time is less than or equal to 24 hours.

* * * * *